US 8,021,670 B2

(12) United States Patent
Drexler et al.

(10) Patent No.: US 8,021,670 B2
(45) Date of Patent: Sep. 20, 2011

(54) VACCINE AGAINST *MYCOPLASMA* PRRSV

(75) Inventors: Christa Sibilla Drexler, Boxmeer (NL); Maarten Witvliet, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 267 days.

(21) Appl. No.: 12/296,438

(22) PCT Filed: Apr. 6, 2007

(86) PCT No.: PCT/EP2007/053420
§ 371 (c)(1),
(2), (4) Date: Oct. 8, 2008

(87) PCT Pub. No.: WO2007/116032
PCT Pub. Date: Oct. 18, 2007

(65) Prior Publication Data
US 2009/0304737 A1 Dec. 10, 2009

Related U.S. Application Data

(60) Provisional application No. 60/791,094, filed on Apr. 10, 2006.

(30) Foreign Application Priority Data

Apr. 10, 2006 (EP) .................................. 06112444

(51) Int. Cl.
*A61K 39/12* (2006.01)
*A61K 39/02* (2006.01)

(52) U.S. Cl. ............... 424/201.1; 424/204.1; 424/264.1; 424/815; 424/825

(58) Field of Classification Search ........................ None
See application file for complete search history.

(56) References Cited

U.S. PATENT DOCUMENTS 5,925,359 A * 7/1999 Van Woensel et al. .... 424/204.1

OTHER PUBLICATIONS

Thacker, E.L. et al. "Effect of vaccination on the potentiation of porcine reproductive and respiratory syndrome virus (PRRSV)-induced pneumonia by *Mycoplasma hyopneumoniae*" Vaccine, 18:1244-1252 (2000).
Boettcher, T.B. et al. "Vaccine efficacy and immune response to *Mycoplasma hyopneumoniae* challenge in pigs vaccinated against porcine reproductive and respiratory syndrome virus and *M hyopneumoniae*" Journal of Swine Health and Production, 10(6):259-264, 2002.

* cited by examiner

*Primary Examiner* — Nita M Minnifield
*Assistant Examiner* — Brian J Gangle
(74) *Attorney, Agent, or Firm* — William M. Blackstone

(57) ABSTRACT

The present invention relates to the use of an immunogenic dose of immunogenic material of *Mycoplasma hyopneumoniae* and an immunogenic dose of live attenuated PRRS virus for the manufacture of a vaccine, and to a vaccine kit comprising such a vaccine.

4 Claims, 1 Drawing Sheet

VACCINE AGAINST *MYCOPLASMA* PRRSV

PRIORITY CLAIM TO RELATED PATENT APPLICATIONS

This patent claims priority under 35 U.S.C. §371 as a national phase of International Patent Application No. PCT/EP2007/053420 (filed Apr. 6, 2007; and published on Oct. 18, 2007 as International Publication No. WO 2007/116032), which, in turn, claims priority to European Patent Application No. 06112444.2 (filed Apr. 10, 2006) and U.S. Patent Application No. 60/791,094 (filed Apr. 10, 2006). The entire text of each of the above-referenced patent applications is hereby incorporated by referenced into this patent.

The present invention relates to the use of an immunogenic dose of immunogenic material of *Mycoplasma hyopneumoniae* and an immunogenic dose of live attenuated PRRS virus for the manufacture of a vaccine, and to a vaccine kit comprising such a vaccine.

BACKGROUND OF THE INVENTION

Mycoplasmal pneumonia of swine caused by the bacterial pathogen *Mycoplasma hyopneumoniae* is a widespread chronic respiratory disease in pigs. Especially young piglets are vulnerable to this, non-fatal, disease. The enzootic pneumonia is a chronic disease that results in poor feed conversion and stunted growth. The disease is highly contagious and transmission is usually through direct contact with infected respiratory tract secretions, e.g. in the form of infected droplets after coughing/sneezing.

The most problematic consequence of this disease is that it predisposes for all kinds of secondary infections of the respiratory system.

It is estimated that e.g. in the USA, 99% of all pig farms are infected. Yearly losses are estimated to be between 100 and 300 million dollars.

Another very frequently encountered respiratory disease in pigs is the disease commonly known as Porcine Reproductive Respiratory Syndrome (PRRS), and as Porcine Epidemic Abortion and Respiratory Syndrome (PEARS). Currently the disease is world-wide referred to as PRRS. The pathology is not restricted to respiratory disease but also to abortion. Other symptoms, usually or occasionally seen with the disease are: off feed, anorexia, bluish discolorations of the extremities, especially the ears.

The causative agent of the disease is now known to be a small enveloped RNA virus. In breeding females, PRRS causes fever, depression, and decreased appetite in sows and gilts. Reproductive problems will follow and affect primarily females in late gestation.

In young pigs, PRRS predominately affects the respiratory system. Abnormally rapid breathing or "thumping" is observed. The severity of problems from other bacterial and viral pathogens often will seem to intensify, with death losses and treatment costs ensuing. Poor performance may follow, with pigs taking extra weeks to finish.

In addition to the frequently seen diseases caused by *Mycoplasma hyopneumoniae* and PRRS virus, currently an economically significant respiratory disorder in pigs is more and more frequently seen. This disorder is characterized by slow growth, decreased feed efficiency, lethargy, anorexia, fever, cough and dyspnea. It is commonly known now as porcine respiratory disease complex (PRDC), and the two most common pathogens isolated from pigs suffering from PRDC are *Mycoplasma hyopneumoniae* and PRRS virus. Apparently, the disease is caused by some combined action of the two pathogens.

The pig farming industry benefits from the presently available efficacious vaccines against *Mycoplasma hyopneumoniae* infection and PRRS virus infection. And since especially young piglets are vulnerable to *Mycoplasma hyopneumoniae* infection as well as PRRS virus infection, it would seem most efficient to vaccinate against both diseases at the same early moment in time.

It has however become evident over the years that this is not an option. It is now an established fact that the efficacy of *Mycoplasma hyopneumoniae* vaccines significantly decreases if pigs become either infected or vaccinated with PRRS virus. This effect is seen if infection or vaccination with PRRS virus takes place during vaccination or even 1-2 weeks after vaccination with a *Mycoplasma hyopneumoniae* vaccine. Even avirulent vaccine strains of PRRS virus show this effect (Pig International 30: 9-12 (2000), Thacker, E. L. et al., J. Clin. Microbiol. 37: 620-627 (1999), Thacker, E. L. et al, Vaccine 18: 1244-1252 (2000)).

In addition, it was shown that PRRS-infection induces a very rapid onset of the pathology of a *Mycoplasma hyopneumoniae* infection.

Moreover, *Mycoplasma hyopneumoniae* infection increases the duration and severity of viral infections in general, such as PRRS (Thacker, E. L. et al., Vaccine 18: 1244-1252 (2000)) and Swine Influenza (Thacker, E. L. et al., J. Cl. Microbiol. 39: 2525-2530 (2001)). This is an additional reason to vaccinate against viral infections such as PRRS and Swine Influenza as soon as possible after birth, but anyway before *Mycoplasma hyopneumoniae* strikes.

Thus, for the reasons mentioned above, there is a strong preference to first vaccinate with PRRS-virus vaccine, instead of applying both a PRRS-virus vaccination and a *Mycoplasma hyopneumonia* vaccination. As a consequence however, one has to wait until the live attenuated PRRS vaccine strain has disappeared from the body. This means that one has to wait for at least two to three weeks and preferably longer, before a first (priming) *Mycoplasma hyopneumonia* vaccine can safely be administered and even four weeks and preferably longer, before giving the second vaccination (booster vaccination) with *Mycoplasma hyopneumonia* vaccine. As another consequence, the piglets will remain unprotected against *Mycoplasma hyopneumonia* infection for at least four weeks after PRRS-vaccination.

However there are currently no ways to circumvent these undesired consequences.

SUMMARY OF THE INVENTION

It is an objective of the present invention to provide a solution to the problem mentioned above.

It was surprisingly found now that if piglets are first vaccinated with *Mycoplasma hyopneumoniae*, followed by a second vaccination with both *Mycoplasma hyopneumoniae* and a live attenuated PRRS virus, they quickly develop an excellent protection against both PRRS virus infection and *Mycoplasma hyopneumoniae* infection and, even more unexpectedly, without significant adverse reactions.

This new approach has the strong advantage above the currently preferred method that within a very short time after birth, piglets can be fully protected against both *Mycoplasma hyopneumoniae* infection and PRRS infection.

Apparently, if an immunogenic dose of immunogenic material of *Mycoplasma hyopneumoniae* and an immunogenic dose of live attenuated PRRS virus are administrated in a combined way, to pigs that have been primed with a *Mycoplasma hyopneumoniae* vaccine, the known problems are circumvented.

DETAILED DESCRIPTION OF THE EMBODIMENTS

Figure 1:
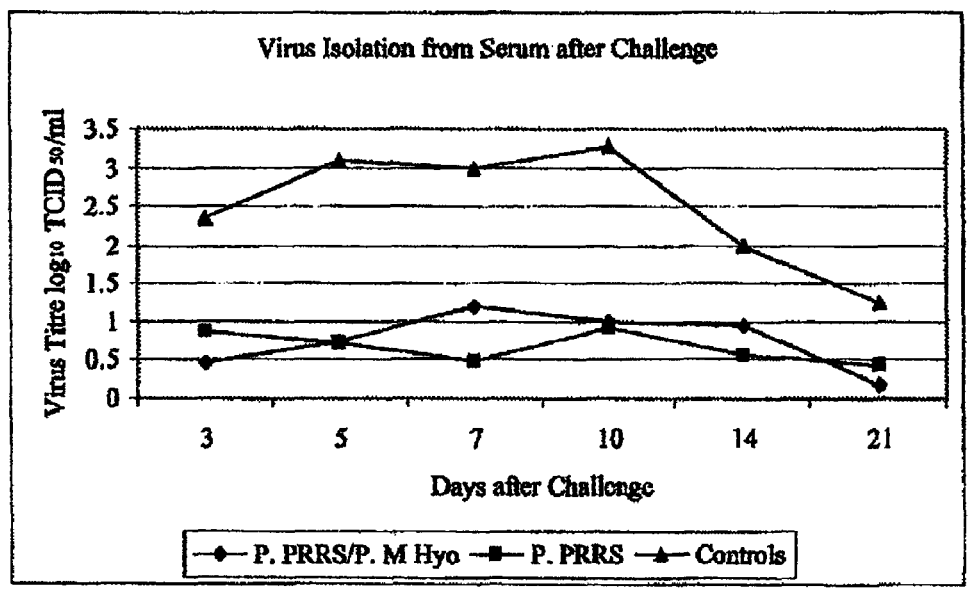
FIG. 1 illustrates the isolation of PRRS virus at time points from 3 to 21 days after challenge in animals immunized with a PRRS/*M.hyo.* vaccine, with a PRRS vaccine and in unvaccinated controls.

The immunogenic material of *Mycoplasma hyopneumoniae* can e.g. be a bacterin, or it can be an immunogenic subunit. It can equally be a live recombinant vector virus or a non-*Mycoplasma hyopneumoniae* bacterial vector capable of expressing genetic material encoding an immunogenic subunit of *Mycoplasma hyopneumoniae.*

An immunogenic dose is known in the art as the amount of immunogenic material that is, possibly in combination with an adjuvant, sufficient to trigger an immune response in the target animal.

Thus, a first embodiment of the present invention relates to the use of an immunogenic dose of immunogenic material of *Mycoplasma hyopneumoniae* and an immunogenic dose of live attenuated PRRS virus for the manufacture of a vaccine for use in the combined administration of *Mycoplasma hyopneumoniae* vaccine and PRRSV vaccine to *Mycoplasma hyopneumoniae* primed pigs.

From an economic point of view, *Mycoplasma hyopneumoniae* bacterins are efficacious, easy to make, safe and inexpensive. Therefore most of the commercially available *Mycoplasma hyopneumoniae* vaccines are based upon bacterins.

Thus, a preferred form of this embodiment relates to the use of an immunogenic dose of *Mycoplasma hyopneumoniae* bacterin and an immunogenic dose of live attenuated PRRS virus for the manufacture of a vaccine for use in the combined administration of *Mycoplasma hyopneumoniae* vaccine and PRRS V vaccine to *Mycoplasma hyopneumoniae* primed pigs.

The expression "bacterin" relates in the art to inactivated bacteria. Such inactivation can e.g. be done by means of chemical treatment such as e.g. formalin treatment, heat treatment, treatment in a French Press and radiation.

A live attenuated PRRS virus is a PRRS virus that is non-pathogenic for the target animal, or exhibits a substantial reduction of virulence compared to the wild-type virus.

Although preferred, the immunogenic material of *Mycoplasma hyopneumoniae* and the live attenuated PRRS virus of the vaccine for use in the combined administration need not necessarily be administrated in a mixed form i.e. mixed together. The reason for this is that the route of administration of each of the active components may differ, depending e.g. on the formulation of the components, the housing of the pigs and farm management. The immunogenic material of *Mycoplasma hyopneumoniae* (also referred to as the *Mycoplasma hyopneumoniae* component) may e.g. be given orally, intra-nasally or by means of injection. The live attenuated PRRS virus (also referred to as the PRRSV component) may e.g. for reasons of efficiency be administered through intradermal application, and not necessarily by intramuscular administration. Therefore, depending on e.g. the circumstances on a farm and on the instructions of the manufacturer of the vaccine, it may well be that the route of administration for the *Mycoplasma hyopneumoniae* and PRRSV components of the vaccine is different. It is clear that in such cases the administration of the *Mycoplasma hyopneumoniae* and PRRSV components necessarily takes place at slightly different moments in time. The advantages of the present invention can however still be achieved if the *Mycoplasma hyopneumoniae* and PRRSV components of the vaccine for use in combined administration are administered within a relatively small interval of time of e.g. less than 24 hours, preferably less than 8 hours. For practical reasons, the interval will in practice preferably be even smaller; less than 4 hours, less than 2 hours, less than one hour, less than 30 minutes, less than 15 minutes, less than 10 minutes, less than 5 minutes or less than 2 minutes, in that order of preference.

Thus, combined administration is considered to be the administration of the *Mycoplasma hyopneumoniae* and PRRSV components within a relatively small interval of time of less than 24 hours, less than 8 hours, less than 4 hours, less than 2 hours, less than one hour, less than 30 minutes, less than 15 minutes, less than 10 minutes, less than 5 minutes or less than 2 minutes, in that order of preference.

A preferred embodiment of the invention relates to the use of an immunogenic dose of immunogenic material of *Mycoplasma hyopneumoniae* and an immunogenic dose of live attenuated PRRS virus for the manufacture of a vaccine for use in the combined administration of *Mycoplasma hyopneumoniae* vaccine and PRRSV vaccine to *Mycoplasma hyopneumoniae* primed pigs, wherein the vaccine for use in combined administration comprises the PRRSV component and the *Mycoplasma hyopneumoniae* component in a mixed form.

Significant differences have been found, in both the antigenic and the genotypic make-up, between European and North American PRRS virus strains. The characteristics of European PRRS virus strains and how they differ from the North American strains are well-known in the art. The differences between European and North American PRRS virus strains have i.a. been described in Meng, X.-J. et al., Arch. Virol. 140: 745-755 (1995), in Suarez, P. et al., Virus Research 42: 159-165 (1996) and in Allende, R. et al., J. Gen Virol. 80: 307-315 (1999). It has become clear in the past years that cross-protection between European and North American PRRS virus strains is insufficient or even non-existent.

Therefore, another preferred form of this embodiment of the present invention relates to the use of an immunogenic dose of immunogenic material of *Mycoplasma hyopneumoniae* and an immunogenic dose of live attenuated PRRS virus for the manufacture of a vaccine for use in the combined administration of *Mycoplasma hyopneumoniae* vaccine and PRRSV vaccine to *Mycoplasma hyopneumoniae* primed pigs, wherein the live attenuated PRRS virus is of a European strain. This is especially advantageous to control and decrease the number of European cases of porcine respiratory disease complex.

In another preferred form of this embodiment, in the manufacturing of the vaccine for use in the combined administration of *Mycoplasma hyopneumoniae* vaccine and PRRSV vaccine there are added one or more antigens derived from other pig pathogenic organisms or viruses, or genetic information encoding such antigens.

Such organisms and viruses are preferably selected from the group of Pseudorabies virus, Porcine influenza virus, Porcine parvo virus, Transmissible gastro-enteritis virus, Rotavirus, *Escherichia coli, Erysipelo rhusiopathiae, Lawsonia intracellularis, Bordetella bronchiseptica, Salmonella cholerasuis, Haemophilus parasuis, Pasteurella multocida, Streptococcus suis, Brachyspira hyodysenteriae* and *Actinobacillus pleuropneumoniae.*

It goes without saying, that in principle bacteria or viruses from this group can in principle also be added to the *Mycoplasma hyopneumoniae* vaccine used for priming, provided that they do not adversely interfere with the beneficial effects of the use according to the invention.

Another embodiment of the present invention relates to a vaccine kit comprising the vaccine for use in the combined administration in a form wherein the *Mycoplasma hyopneumoniae* component is present in one container, preferably in suspension, and the PRRSV component is present in a second container, preferably in a freeze-dried form. The advantage of such a kit is the following; the *Mycoplasma hyopneumoniae* component can be aspirated from the first container through the needle of a syringe and subsequently be added to the second container to dissolve the freeze-dried PRRSV component. This mixture would then be ready for combined administration.

Alternatively, the vaccine kit comprises a vaccine for use in combined administration wherein the PRRSV component and the *Mycoplasma hyopneumoniae* component are in one container. Such a container can e.g. be a vaccine vial. If the said components are in the same container they need not necessarily be mixed already. They can e.g. be separated by a barrier, e.g. a membrane before administration. At the moment of administration, the needle of the syringe for administration can punch the membrane where-after the components will mix. They can subsequently be used as a mixture to fill the syringe and be administered as a mixture. The components can also be present as separated freeze-dried cakes or freeze-dried bodies in one and the same vial. The addition of a diluent would then induce the mixing of the components prior to administration.

Therefore another form of this embodiment relates to a vaccine kit that comprises a vaccine for use in the combined administration of immunogenic material of *Mycoplasma hyopneumoniae* and live attenuated PRRS virus according to the invention wherein the *Mycoplasma hyopneumoniae* component and the PRRSV component are present in one single container.

*Mycoplasma hyopneumoniae* primed pigs are pigs that were vaccinated with a *Mycoplasma hyopneumoniae* vaccine prior to the combined administration of a *Mycoplasma hyopneumoniae* and a PRRSV vaccine. As a result of the priming vaccination of the pigs a primary immune response against *Mycoplasma hyopneumoniae* builds up. Development of such an immune response needs some time. However for the vaccine for use in the combined administration of *Mycoplasma hyopneumoniae* and PRRS virus to develop its efficacy, an adequate priming reaction against *Mycoplasma hyopneumoniae* needs to be present. Therefore, preferably, the vaccine for use in combined administration of *Mycoplasma hyopneumoniae* and PRRS virus would be administered 7 or more days after the priming of the pig.

The combined administration of *Mycoplasma hyopneumoniae* and PRRSV vaccine would preferably be done within 35 days after priming, more preferably within 14-35 days after priming: as long as the vaccine for use in combined administration of *Mycoplasma hyopneumoniae* (booster vaccination) and PRRS virus is not administered, the pigs are not fully protected against *Mycoplasma hyopneumoniae* infection and not against PRRS virus infection. Thus, preferably, the administration of the vaccine for use in combined administration is done between 7 and 35 days after *Mycoplasma hyopneumoniae* priming, more preferably between 14 and 35 days, even more preferably between 21 and 28 days after *Mycoplasma hyopneumoniae* priming.

It goes without saying that for the priming of the pigs to be vaccinated, by far most *Mycoplasma hyopneumoniae* vaccines are suitable.

Mycoplasma vaccines have been disclosed in e.g. PCT-Application WO 91/18627, U.S. Pat. No. 5,338,543 and European Patent EP 550.477.

Such vaccines, mainly bacterins, are also easily commercially available from various manufacturers. Examples of commercially available *Mycoplasma hyopneumoniae* vaccines are PORCILIS® M HYO, PROSYSTEMS® M (PORCILIS® M) (Intervet Int. B.V.), PROSYSTEM® BPM, (PORCILIS®) (Intervet in B.V.), RESPISURE® (Pfizer), STELLAMUNE® (Pfizer), SUVAXYNE® M. HYO (Fort Dodge), HYORESP® (Merial) and M+PAC® (Schering-Plough).

For the *Mycoplasma hyopneumoniae* component that is used in the manufacture of the vaccine for use in the combined administration according to the invention, the same goes. Mycoplasma vaccines as disclosed in e.g. PCT-Application WO 91/18627, U.S. Pat. No. 5,338,543 and European Patent EP 550.477 can readily be used. In principle, commercially available Mycoplasma vaccines such as described above are also suitable.

With regard to the PRRSV-component of the vaccine for use in the manufacture of the vaccine for use in the combined administration according to the invention, live attenuated PRRS vaccines as disclosed in i.a. European patents EP 676.467, EP 835.930, U.S. Pat. Nos. 5,510,258 and 5,587,164 can readily be used. In principle, commercially available PRRS vaccines such as those available from e.g. Intervet Int. B.V., e.g. PORCILIS® PRRS can also efficiently be used.

Therefore, the skilled person would not experience any problems in selecting the *Mycoplasma hyopneumoniae* component and the live attenuated PRRS component that form the basic components necessary for the manufacture of the vaccine for use in the combined administration according to the invention, nor would he experience any problems in selecting the *Mycoplasma hyopneumoniae* vaccine for the priming.

The skilled person would know how to administer the vaccines. Both the dose and the routes of administration of the *Mycoplasma hyopneumoniae* vaccine and the live attenuated PRRS vaccine evidently follow from the directions as given by the manufacturer in case components of a commercial vaccine are used or, in case of a non-commercial vaccine, from the methods e.g. disclosed in any of the patents mentioned above.

Merely as an example: if the skilled artisan chooses PORCILIS® M HYO as the *Mycoplasma hyopneumoniae* vaccine and PORCILIS® PRRS as the PRRS vaccine, a priming with a 2 ml dose would preferably be given at 5-9 days of age, and the administration of the vaccine for use in the combined administration of *Mycoplasma hyopneumoniae* vaccine and live attenuated PRRSV vaccine according to the invention would preferably be done at 23-30 days of age.

Another embodiment of the present invention thus relates to a method for the vaccination of pigs against infection with PRRS virus and *Mycoplasma hyopneumoniae*, wherein that method comprises the steps of administering a first (a priming) vaccination with a *Mycoplasma hyopneumoniae* vaccine, followed by combined vaccination with immunogenic material of *Mycoplasma hyopneumoniae* and a live attenuated PRRS virus. The combined vaccination thus functions with regard to the immunogenic material of *Mycoplasma hyopneumoniae* as a second (a booster) vaccination.

The beneficial effect of a vaccine for use in the combined administration of *Mycoplasma hyopneumoniae* vaccine and PRRSV to *Mycoplasma hyopneumoniae* vaccine primed pigs is illustrated by (but not restricted to) the Examples given below.

EXAMPLES

Example 1

The efficacy of the simultaneous use of a *M. hyopneumoniae* bacterin PORCILIS® M HYO and a modified live PRRS vaccine PORCILIS® PRRS was tested in a vaccination-challenge experiment in SPF piglets according to the following experimental design:

| group | n | 1st vaccination at 1 week of age | 2nd vaccination at 4 weeks of age | challenge |
|---|---|---|---|---|
| 1 | 12 | M. hyo | M. hyo + PRRS | *M. hyopneumoniae* |
| 2 | 12 | M. hyo | M. hyo | at 6 weeks of age |
| 3 | 12 | — | — | |
| 4 | 7 | M. hyo | M. hyo + PRRS | PRRSV |
| 5 | 6 | — | PRRS | at 8 weeks of age |
| 6 | 6 | — | — | |

The *M. hyopneumoniae* vaccine was given as a 2 ml intramuscular dose and the lyophilized PRRS vaccine strain was also given as a 2 ml intramuscular dose after reconstitution in diluent (DILUVAC FORTE™, Intervet Int. B. V., Wim de Korverstraat 35, Boxmeer, the Netherlands) (group 5) or in the *M. hyopneumoniae* vaccine (groups 1 and 4). During the experiment, a number of piglets died for reasons unrelated to vaccination or challenge infection.

Challenge with *M. hyopneumoniae* was performed by intratracheal inoculation of the piglets with $10^{8.5}$ CCU of a culture of a low passage *M. hyopneumoniae* field isolate on two consecutive days. Three weeks after challenge, the pigs were necropsied and consolidated lung lesions were scored according to Goodwin & Whittlestone (British Vet. Journ. 129: 456-464 (1973)). Reduction of *M. hyopneumoniae*-specific lung lesions was statistically significant for both groups 1 and 2 compared to the controls. The difference between groups 1 and 2 was not statistically significant (p=0.83, Mann-Whitney U-test).

| group | N | 1st vaccination at 1 week of age | 2nd vaccination at 4 weeks of age | *M. hyopneumoniae* lesion score* |
|---|---|---|---|---|
| 1 | 12 | M. hyo | M. hyo + PRRS | $3.7^a$ |
| 2 | 11 | M. hyo | M. hyo | $5.9^a$ |
| 3 | 11 | — | — | $13.4^b$ |

*maximum lesion score is 55; groups with different superscripts are significantly different (p < 0.05, Mann-Whitney U-test)

PRRSV challenge was performed by intranasal installation of $10^5$ $TCID_{50}$ in 1 ml PBS per nostril of a wild-type PRRSV strain. On days 3, 5, 7, 10, 14 and 21 post challenge, blood samples were taken from all piglets for virus titration on pig alveolar macrophages (PAM). Briefly, monolayers of PAM in 96-well plates were inoculated with 10-fold serial dilutions of the serum samples in quadruplicate followed by incubation at 37° C. for 7 days. Cells were monitored daily for CPE and the virus titer was expressed as $TCID_{50}$/ml according to the method of Reed and Muench. On all sampling days, titers of the challenge virus were significantly lower in the vaccinated groups 4 and 5. The level of protection in groups 4 and 5 was not different.

Example 2

The efficacy of the simultaneous use of a *M. hyopneumonia* bacterin (PORCILIS® M HYO) and a modified live PRRS vaccine (PORCILIS PRRS) against *M. hyopneumonia* was also tested in commercial piglets:

Please amend the Specification by adding FIG. 1 on a separate page submitted herewith. FIG. 1 is the same as the figure now deleted from page 12.

| group | N | 1st vaccination at 1 week of age | 2nd vaccination at 4 weeks of age | challenge |
|---|---|---|---|---|
| 1 | 12 | M. hyo | M. hyo + PRRS | *M. hyopneumoniae* |
| 2 | 12 | — | PRRS | at 6 weeks of age |
| 3 | 12 | M. hyo | M. hyo | |
| 4 | 12 | — | — | |

The *M. hyopneumoniae* vaccine was given as a 2 ml intramuscular dose and the lyophilized PRRS vaccine strain was also given as a 2 ml intramuscular dose after reconstitution in diluent (group 2) or in the *M. hyopneumoniae* vaccine (group 1) During the experiment, one piglet of group 2 was euthanized before vaccination because of poor general health and several piglets in groups 2, 3 and 4 had to be excluded from lesion scoring because of severe pleuritis.

Challenge with *M. hyopneumoniae* was performed by intratracheal inoculation of the piglets with $10^{8.5}$ CCU of a culture of a low passage *M. hyopneumoniae* field isolate on two consecutive days. Three weeks after challenge, the pigs were necropsied and consolidated lung lesions were scored according to Goodwin & Whittlestone. Reduction of *M. hyopneumoniae* specific lung lesions was statistically significant for both groups 1 and 3. The difference between group 1 and 3 was not statistically significant (p=0.13, Mann-Whitney U-test).

| group | n | 1st vaccination at 1 week of age | 2nd vaccination at 4 weeks of age | *M. hyopneumoniae* lesion score* |
|---|---|---|---|---|
| 1 | 12 | M. hyo | M. hyo + PRRS | $1.3^a$ |
| 2 | 9 | — | PRRS | $11.7^b$ |
| 3 | 11 | M. hyo | M. hyo | $2.4^a$ |
| 4 | 9 | — | — | $6.6^b$ |

*maximum lesion score is 55; groups with different superscripts are significantly different (p < 0.05, Mann-Whitney U-test)

The invention claimed is:

1. A method for the vaccination of pigs against infection with Porcine Reproductive Respiratory Syndrome (PRRS) virus and *Mycoplasma hyopneumoniae*, said method comprising the steps of administering first a priming vaccination with a vaccine comprising immunogenic material of *Mycoplasma hyopneumoniae*, followed by combined vaccination with a vaccine comprising immunogenic material of *Mycoplasma hyopneumoniae* and a live attenuated PRRS virus, wherein said priming vaccination is with a vaccine that contains no live PRRS virus.

2. The method of claim 1, wherein said immunogenic material of *Mycoplasma hyopneumoniae* is a *Mycoplasma hyopneumoniae* bacterin.

3. The method of claim 1, wherein the live attenuated PRRS virus is of a European strain.

4. The method of claim 1, wherein the vaccine used in combined administration comprises the live attenuated PRRS virus and the immunogenic material of *Mycoplasma hyopneumoniae* in a mixed form.

* * * * *